(12) United States Patent
Schott et al.

(10) Patent No.: US 6,787,525 B1
(45) Date of Patent: Sep. 7, 2004

(54) GLYCERYL NUCLEOTIDES, METHOD FOR THE PRODUCTION THEREOF AND THEIR USE

(76) Inventors: Herbert Schott, Hartmeyerstr. 14, D-72076, Tübingen (DE); Peter Stephan Ludwig, Lilienstr. 3, D-72764, Reutlingen (DE)

(*) Notice: Subject to any disclaimer, the term of this patent is extended or adjusted under 35 U.S.C. 154(b) by 0 days.

(21) Appl. No.: 09/856,165

(22) PCT Filed: Dec. 3, 1999

(86) PCT No.: PCT/EP99/09461
§ 371 (c)(1),
(2), (4) Date: Jan. 12, 2001

(87) PCT Pub. No.: WO00/34298
PCT Pub. Date: Jun. 15, 2000

(30) Foreign Application Priority Data

Dec. 4, 1998 (DE) .......................................... 198 55 963

(51) Int. Cl.$^7$ .......................... A61K 31/70; C07H 21/00
(52) U.S. Cl. ............................. 514/45; 514/47; 514/51; 514/24; 514/81; 514/86; 536/26.3; 544/243; 544/264
(58) Field of Search .................... 536/26.3; 544/243, 544/264; 514/45, 47, 24, 51, 81, 86

(56) References Cited

FOREIGN PATENT DOCUMENTS

| EP | 0 457 570 A1 | 11/1991 |
|---|---|---|
| JP | 03-236 396 A | * 10/1991 |
| WO | WO 93 16093 A1 | 8/1993 |
| WO | WO 98 28978 A1 | 7/1998 |
| WO | WO 98 38202 A1 | 9/1998 |

OTHER PUBLICATIONS

Benner et al., "Oligonucleotides Containing Flexible Nucleoside Analogues," *J. American Chemical Society*, 112(1), 453–455 (Jan. 3, 1990).*
Romanova et al., "The Synthesis and Properties of DNA-Duplexes with 9-[1'-hydroxy-2'-(hydroxymethyl)ethoxy] methylguanine," *Bioorganicheskaya Khimya*, 17(12), 1640–1648 (1991); *Chemical Abstracts*, 116(23), p. 876, Abstract No. 236054k (Jun. 8, 1992).*

Vergeles et al., "High Efficiency of Glycerol 2–Phosphate and sn–glycerol 3–phosphate as Nucleotidyl Acceptors in Snake Venom Phosphodiesterase Esterifications," *European Journal of Biochemistry*, 233(2), 442–447 (Oct. 15, 1995).*
Peyman et al., "Facile Preparation of 3'–Derivatized Oligodeoxynucleotides," *Bioorganic & Medicinal Chemistry*, 5(21), 2469–2472 (Nov. 2, 1995).*
Antsypovich et al., "Synthesis of Modified Oligonucleotides and Their Duplexes with Covalently LInked Strands," *Bioorganicheskaya Khimya*, 21(10), 774–780 (1995); *Chemical Abstracts*, 127(20), p. 724, Abstr. No. 278389f (Nov. 17, 1997).*

* cited by examiner

Primary Examiner—James O. Wilson
Assistant Examiner—Lawrence E. Crane
(74) *Attorney, Agent, or Firm*—Bacon & Thomas

(57) ABSTRACT

The invention relates to glyceryl nucleotides of the formula Ia

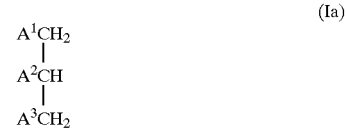

in which
a) one of the radicals $A^1$, $A^2$ and $A^3$ is a hydrogen atom or a radical selected from hydroxyl, mercapto, alkyl, alkenyl, polyoxyalkenyl, aryl, acyl, alkyloxy, alkenyloxy, polyoxyalkenyloxy, acyloxy, aryloxy, alkylthio, alkenylthio, acylthio and arylthio, where the alkyl, alkenyl and acyl radicals are optionally substituted by from 1 to 3 aryl radicals; and
b1) two of the remaining radicals $A^1$, $A^2$ and $A^3$ are two nucleoside groups which are different from each other; or
b2) one of the remaining radicals $A^1$, $A^2$ and $A^3$ is a nucleoside group and the other of the remaining radicals is a hydroxycarbonyl group,
where at least one of the nucleoside groups is not a naturally occurring nucleoside group;
to processes for preparing these compounds, to pharmaceutical remedies which comprise these compounds, and to the use of these compounds for treating cancer diseases and infectious diseases.

14 Claims, No Drawings

GLYCERYL NUCLEOTIDES, METHOD FOR THE PRODUCTION THEREOF AND THEIR USE

The present invention relates to the novel, where appropriate amphiphilic, glyceryl nucleotides, to their preparation and to compositions for treating cancer diseases and infectious diseases.

Nucleoside analogs which exhibit defined structural features have proved to be valuable drugs in the chemotherapy of cancer diseases and infectious diseases caused by viruses (Advanced Drug Delivery Review (1996) 19, 287). However, the therapeutic effect of the nucleoside analogs is only seen when the nucleoside analogs, which are themselves inactive, are taken up by the cell, as prodrugs, and then anabolized into the actual active compounds, i.e. the 5'-triphosphate derivatives of the nucleoside analog. These nucleotides stop DNA replication and/or block the reverse transcriptase. Nucleoside analogs, such as 1-β-D-arabinofuranosylcytosine (araC) and 5-fluoro-2'-deoxyuridine (5FdU), which prevent DNA replication, are effective against malignant diseases of the hematopoietic cells and against solid tumors. Dideoxynucleoside analogs, such as 3'-azido-2',3'-dideoxythymidine (AZT), 2',3'-dideoxycytidine (ddC), 2',3'-dideoxyinosine (ddI), 3'-thia-2',3'-dideoxycytidine (3TC) and 2',3'-didehydro-2',3'-dideoxythymidine (d4T), are particularly suitable for the therapy of infection with HIV.

A nonnucleosidic antiviral active compound, such as the trisodium salt of phosphonoformic acid (Foscarnet) blocks the pyrophosphate-binding site of the viral polymerase. This prevents viruses such as herpes simplex virus, HIV virus and human cytomegalovirus from replicating. Amphiphilic glyceryl derivatives of Foscarnet, which are better able to traverse the membrane, contribute to optimizing the virus therapy (Antivir. Chem. & Chemother. (1998) 9, 33).

Because of the development of resistance during the course of chemotherapy, which occurs particularly rapidly in the case of HIV treatment, the progression of the disease can only be retarded in the long term by using a combination therapy. In such a therapy, several antiviral active compounds are administered jointly (Schweiz. Med. Wochenschr. (1997) 127, 436). Because the therapy regime which has to be imposed on the patients in the case of combination therapy is strict, patient compliance is low. The therapeutic success which is achieved is therefore well below the possible success which could be achieved with the high potential which the available drugs possess. (AIDS 1998 Diagnostik und Therapie (Diagnosis and Therapy, Steinhauser publishing company).

At best, administration of a form in which, for example, the two nucleosidic prodrugs (AZT and 3TC) are present as a mixture, as is the case with Combivir, only makes combination therapy more practicable for patients. However, it is scarcely possible to achieve an improved effect with such mixtures since the uptake of the prodrugs by the cell is not increased and nor is there any optimization of their anabolism to give the active compound.

On the other hand, it is possible to optimize combination therapy decisively using amphiphilic combination preparations in which two antiviral nucleoside analogs are coupled by way of a phosphodiester bond (EP 0 642 527 B 1). A certain disadvantage of these ampiphilic dinucleoside phosphate analogs is that, when a desired enzymatic cleavage of the phosphodiester bond takes place, only one monomer unit is in each case released as an active nucleotide analog whereas the second monomer unit of the combination preparation inevitably remains as a nucleoside analog which is in itself inactive. If the cell does not anabolize this nucleoside analog to give the active nucleotide analog, up to 50% of the administered dimer can then not be used therapeutically and is consequently inactive. An additional disadvantage of these amphiphilic combination preparations is that at least one of the two coupled nucleoside analogs has to possess a lipophilic radical so as to ensure that the resulting dimer is amphiphilic. Consequently, two nucleoside analogs which are suitable for combination therapy, but neither of which can be lipophilized, cannot be converted into amphiphilic dimers and used as a combination preparation in therapy.

The object of this invention is to make available novel combination preparations which can be used to combat cancer diseases and infections even more effectively. This object is achieved by means of novel glyceryl nucleotides which, on being metabolized, are in each case able to liberate two active compounds simultaneously such that the advantages of the abovementioned combination of two active compounds are fully exploited. In order to prepare the novel glyceryl nucleotides, preference is given to covalently bonding either two therapeutically active nucleoside derivatives to each other, or a nucleoside derivative to phosphonoformic acid or its salt form (Foscarnet), by way of a glycerol lipid backbone.

The invention firstly relates to glyceryl nucleotides of the formula Ia

in which
a) one of the radicals $A^1$, $A^2$ and $A^3$ is a hydrogen atom, or a radical which is selected from hydroxyl, mercapto, alkyl, alkenyl, polyoxyalkenyl, aryl, acyl, alkyloxy, alkenyloxy, polyoxyalkenyloxy, acyloxy, aryloxy, alkylthio, alkenylthio, acylthio and arylthio, where the alkyl, alkenyl and acyl are optionally substituted by 1 to 3 aryl radicals; and
b1) two of the remaining radicals $A^1$, $A^2$ and $A^3$ are two nucleoside groups which differ from each other, each of which nucleoside groups is linked to the carbon atom of the glyceryl chain by way of a physiologically cleavable phosphorus-containing bridging group; or
b2) one of the remaining radicals $A^1$, $A^2$ and $A^3$ is a nucleoside group and the other of the remaining radicals is a hydroxycarbonyl group, each of which is linked to the carbon atom of the glyceryl chain by way of a physiologically cleavable phosphorus-containing bridging group;

where at least one of the nucleoside groups is not a naturally occurring nucleoside group, which nucleoside group is optionally substituted, in its base moiety, on one or more ring atoms and/or on one or more side groups, such as amino side groups, by one or more radicals which are selected from hydroxyl, amino, halogen, alkyl, alkenyl, polyoxyalkenyl, aryl, acyl, alkyloxy, alkenyloxy, polyoxyalkenyloxy, acyloxy, aryloxy, alkylthio, alkenylthio, acylthio and arylthio, where the alkyl, alkenyl and acyl radicals are optionally substituted by 1 to 3 aryl radicals or halogen atoms; and which nucleoside group is optionally substituted, once or more than once, in its carbohydrate moiety, by substituents which are selected from hydrogen, halogen, such as F, Cl, Br and I, hydroxyl, ethynyl and azido, optionally possesses a heteroatom, which is selected from S, N and O, in place of a carbon atom, and optionally contains one or two non-adjacent C=C double bonds;

in racemic or enantiomerically pure form, and to the pharmaceutically tolerated salts of these compounds.

The nucleoside groups which do not occur naturally and which are present in the compounds according to the invention are derived from nucleosides (nucleoside derivatives) which comprise a heterocyclic radical (base moiety) which is linked N-glycosidically or O-glycosidically to a sugar radical (carbohydrate moiety). They differ from the naturally occurring nucleosides, adenosine, guanosine, cytidine, uridine and thymidine and the corresponding deoxynucleosides in the carbohydrate moiety and/or in the base moiety.

The sugar radical of the nucleoside or nucleoside derivative which does not occur naturally is derived from a hexose or heptose, preferably from a pentose, such as deoxyribose or ribose. Where appropriate, single or several protons or hydroxyl groups can be substituted or eliminated in the sugar radical. In this connection, suitable substituents are selected from the abovementioned substituents hydrogen, halogen, such as F, Cl, Br and I, hydroxyl, ethynyl and azido. Where appropriate, a heteroatom, selected from S, N and O, can be present in place of a carbon atom, and, where appropriate, the sugar radical can contain one or two non-adjacent C=C double bonds.

The base moiety of the nucleoside or nucleoside derivative which does not occur naturally is the radical of a mononuclear or binuclear heterocyclic base which is composed of one or two four- to seven-membered rings which, together, contain at least one ring heteroatom, such as one to six heteroatoms which are selected from N, S and O, in particular N and O. Examples of such bases are the purine and pyrimidine bases adenine, guanine, cytosine, uracil and thymine. Other examples of usable bases are pyrrole, pyrazole, imidazole, aminopyrazole, 1,2,3-triazole, 1,2,4-triazole, tetrazole, pentazole, pyridone, piperidine, pyridine, indole, isoindole, pyridazine, indoxyl, isatin, pyrazine, piperazine, gramine, tryptophan, kynurenic acid, tryptamine, 3-indoleacetic acid, carbazole, indazole, 1,3,5-triazine, 1,2,4-triazine, 1,2,3-triazine and tetrazine. Preferred bases are adenine, guanine, cytosine, uracil and thymine; and also 1,2,3-triazole, 1,2,4-triazole and tetrazole. Where appropriate, said bases can be substituted once or more than once, such as once to four times, in particular once or twice, by the abovementioned radicals hydroxyl, amino, halogen, alkyl, alkenyl, polyoxyalkenyl, aryl, acyl, alkyloxy, alkenyloxy, polyoxyalkenyloxy, acyloxy, aryloxy, alkylthio, alkenylthio, acylthio or arylthio, where the alkyl, alkenyl and acyl radicals are optionally substituted by 1 to 3 aryl radicals or halogen atoms. In this connection, the substitution can take place on a ring heteroatom or, preferably, on a ring carbon atom or a side group, for example an amino side group of the base.

In the compounds of the formula (Ia) according to the invention, the physiologically cleavable, phosphorus-containing bridging groups are preferably derived from phosphodiester groups and their sulfur-containing analogs. In a preferred embodiment, those compounds of the formula Ia are therefore prepared in which nucleoside groups are linked, independently of each other, to the glyceryl radical byway of a bridging group selected from —OP(OZ)(O)O—, —SP(OZ)(O)O—, —OP(OZ)(S)O— and —SP(OZ)(S)O—, and the hydroxycarbonyl group is linked to the glyceryl radical by way of a bridging group selected from —OP(OZ)(O)—, —SP(OZ)(O)— and —SP(OZ)(S)—, in which Z is a proton or a pharmaceutically tolerated cation.

Particular preference is given to those compounds of the formula Ia in which $A^1$, $A^2$ and $A^3$ are selected such that an amphiphilic character is imparted to the molecule. This is achieved by substituting the glyceryl radical or the nucleoside derivative radical(s) by a lipophilic substituent. In this connection, the nucleoside derivative radical preferably carries the lipophilic radical on the base moiety. Examples of such lipophilic radicals which may be mentioned are alkyl, alkenyl, polyoxyalkenyl, aryl, acyl, alkyloxy, alkenyloxy, polyoxyalkenyloxy, acyloxy, aryloxy, alkylthio, alkenylthio, acylthio and arylthio, where the alkyl, alkenyl and acyl radicals are optionally substituted by 1 to 3 aryl radicals or halogen atoms.

The lipophilic radical should preferably comprise more than 6, for example 7 to 30 or 10 to 24, carbon atoms.

Examples of suitable aryl radicals which may be mentioned are: phenyl, naphthyl and benzyl.

Examples of suitable alkyl radicals which may be mentioned are straight-chain or branched radicals having from 1 to 24 C atoms, such as methyl, ethyl, i- or n-propyl, n-, i-, sec- or tert-butyl, n- or i-pentyl; and, in addition, n-hexyl, n-heptyl, n-octyl, n-nonyl, n-decyl, n-undecyl, n-tridecyl, n-tetradecyl, n-pentadecyl and n-hexadecyl, octadecyl, docosanyl, and also the singly or multiply branched analogs thereof.

Examples of suitable alkenyl radicals are the singly or multiply, preferably singly or doubly, unsaturated analogs of the abovementioned alkyl radicals having from 2 to 24 carbon atoms, where the double bond can be located in any position in the carbon chain.

Examples of suitable polyoxyalkenyl radicals are derived from $C_2$–$C_4$-alkylene oxides, which can comprise from 2 to 12 repeating alkylene oxide units.

Examples of suitable acyl radicals are derived from straight-chain or branched $C_1$–$C_{24}$-monocarboxylic acids which are optionally unsaturated once or more than once and optionally substituted. For example, usable acyl radicals are derived from the following carboxylic acids: saturated acids, such as formic, acetic, propionic and n- and i-butyric acid, n- and i-valeric acid, caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotinic acid and melissic acid; singly unsaturated acids, such as acrylic acid, crotonic acid, palmitoleic acid, oleic acid and erucic acid; and doubly unsaturated acids, such as sorbic acid and linoleic acid. If the fatty acids contain double bonds, the latter can then be present either in the cis or trans form.

Examples of suitable alkyloxy, acyloxy, aryloxy, alkenyloxy and polyoxyalkyleneoxy radicals are the oxygen-terminated analogs of the abovementioned alkyl, acyl, aryl, alkenyl and polyoxyalkylene radicals.

Examples of suitable alkylthio, alkenylthio, acylthio and arylthio are the corresponding sulfur-terminated analogs of the above alkyloxy, alkenyloxy, acyloxy and aryloxy radicals.

The invention relates, in particular, to preferably amphiphilic glyceryl nucleotides of the formula I

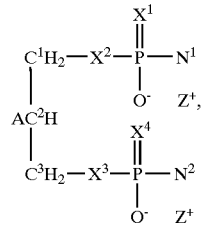

(I)

in racemic and enantiomerically pure form, in which the radical A and the two phosphoric acid residues can be linked, in aryl arbitrary sequence, to the C atoms $C^1$, $C^2$ and $C^3$ of the glycerol backbone;

$X^1$, $X^2$, $X^3$ and $X^4$ are identical or different and are oxygen and sulfur;

A is alkyl, hydroxyl, thiol or an alkoxy, alkylthio, alkylcarboxy or alkylthiocarboxy group, where the alkyl radicals are linear or branched, possess 1–24 C atoms and up to 2 double bonds; and can be substituted by from 1 to 3 aromatic radicals;

Z is hydrogen or the corresponding salt of the acid form of this compound;

$N^1$ or $N^2$ is hydroxycarbonyl or its salt form; and the other of the $N^1$ and $N^2$ radicals is a D- or L-configured nucleoside derivative of the formula II, III and IV, and the two radicals $N^1$ and $N^2$ are different when they are both a D- or L-configured nucleoside derivative of the formulae II, III, and IV,

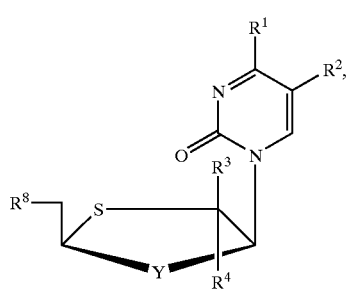

(II)

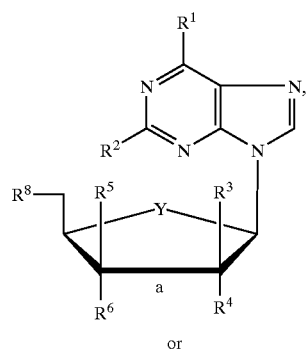

(III)

or

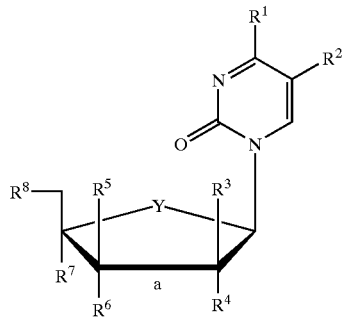

(IV)

where
Y is oxygen or sulfur;
$R^1$ is a hydroxyl, amino, acylated, alkylated or polyoxyethylene-substituted amino group, whose acyl or alkyl radical is linear or branched, possesses 1–24 C atoms and up to 2 double bonds, and can be substituted by an aromatic radical;
$R^2$ is hydrogen, halogen, an amino or hydroxyl group, a bromovinyl group or a linear or branched $C_1$ to $C_{24}$ alkyl radical;
$R^3$, $R^4$, $R^5$, $R^6$, $R^7$ and $R^8$ are identical or different and are hydrogen, halogen, hydroxyl, ethynyl or azido;
and one of the radicals $R^3$ to $R^8$ is oxygen, by way of which the nucleoside derivative is linked to the glyceryl phosphate, and two of the radicals $R^3$ to $R^6$ are dispensed with when a is a C=C double bond.

The radicals A, $R^1$ and $R^2$ in formula I are preferably selected such that a compound having an amphiphilic character is obtained.

If A is an alkoxy radical, preference is then given to radicals having from 12 to 24 C atoms, such as the hexadecyloxy radical, the octadecyloxy radical or the docosanyloxy radical.

If A is a carboxylic acid radical, preference is then given to radicals having from 12 to 24 C atoms, such as the palmitic acid radical, the stearic acid radical or the behenic acid radical.

If A is an alkyl radical, preference is then given to radicals having from 12 to 24 C atoms, such as the hexadecyl radical, the 9octadecenyl radical, the octadecyl radical or he docosanyl radical.

If $R^1$ is an alkylated amino group, its alkyl radical is then preferably a radical having from 12 to 24 C atoms, such as a hexadecyl radical or an octadecyl radical; if $R^1$ is an acylated amino group, the acyl radical is then preferably a radical having from 12 to 24 C atoms, such as a palmitoyl radical, an oleoyl radical or a behenoyl radical.

$R^2$ is preferably hydrogen, halogen, methyl or ethyl; $R^3$, $R^4$, $R^5$, $R^6$ and $R^7$ are preferably azido, hydrogen, fluorine, ethynyl or hydroxyl; and $R^8$ is preferably a hydroxyl group. However, $R^8$ is particularly preferably an oxygen atom by way of which the nucleoside radical is bonded to the P atom of the bridging group.

If one of the two radicals $N^1$ and $N^2$ is a hydroxycarbonyl radical, preference is then given to the other radical being a nucleoside derivative of the formula II or IV.

Other preferred groups of compounds are:
a) compounds of formula (I), in which
$X^1$, $X^2$, $X^3$ and $X^4$ are an oxygen atom;
the $C^1$ atom of the glycerol backbone of the formula I is linked to the radical A, where A is hydroxyl, octadecyl, octadecyloxy, docosyloxy or behenoyloxy, palmitoyl or oleoyl;

the $C^2$ atom of the glycerol backbone of the formula I is linked to $N^2$ by way of a phosphodiester bridge, where $N^2$ is a nucleoside derivative radical of the formula II, III or IV, in which
Y is an oxygen atom;
$R^1$ is a hydroxyl, amino, octadecylamino, docosylamino, palmitoylamino, oleoylamino or behenoylamino group;
$R^2$ is methyl, ethyl, hydrogen or halogen;
$R^3$ to $R^8$ possess the abovementioned meanings, where one of the radicals
$R^3$, $R^4$, $R^5$, $R^6$ and $R^8$ is an oxygen atom by way of which the nucleoside derivative radical $N^2$ is linked to the phosphorus atom, and
the $C^3$ atom of the glycerol backbone of the formula I is linked to the hydroxycarbonylphosphonate radical in its free or salt form.
b) Compounds of the formula I according to group a), in which, in particular,
$N^2$ is a nucleoside derivative radical of the formula II or IV, in which
$R^1$ is an amino, palmitoylamino or hydroxyl group;
$R^2$ is hydrogen, methyl or ethyl;
$R^3$, $R^4$, R and $R^7$ are hydrogen;
$R^6$ is hydrogen, fluorine or azido, and
$R^8$ is an oxygen atom by way of which the $N^2$ is linked to the phosphorus atom.
c) Compounds of formula I, in which
$X^1$, $X^2$, $X^3$ and $X^4$ are an oxygen atom;
A is palmitoyloxy, oleoyoxyl or octadecyloxy and is linked to the $C^2$ atom of the glycerol backbone of the formula I, and
$N^1$ and $N^2$ are different and are a nucleoside derivative radical of the formulae II, III and IV.
d) Compounds of the formula I according to group c), in which, in particular,
$N^1$ is a, preferably L-configured, nucleoside derivative radical of the formula
in which
$R^1$ is an amino or palmitoylamino group;
$R^2$, $R^3$ and $R^4$ are hydrogen, and
$R^8$ is an oxygen atom by way of which the $N^1$ is linked to the phosphorus atom in position $C^1$ or $C^3$ of the glyceryl diphosphate backbone of the formula I;
and $N^2$ is a nucleoside derivative radical of the formula III or IV.
e) Compounds of the formula I according to group c), in which, in particular,
$N^2$ is a nucleoside derivative radical of the formula IV in which
$R^1$ is an amino, palmitoylamino or hydroxyl group;
$R^2$ is hydrogen or methyl;
$R^3$, $R^4$, $R^5$ and $R^7$ are hydrogen;
$R^6$ is hydrogen, fluorine or azido, and
$R^8$ is an oxygen atom by way of which the $N^2$ is linked to the phosphorus atom in position $C^1$ or $C^3$ of the glyceryl diphosphate backbone of the formula I.
f) Compounds of the formula I according to group c), in which, in particular,
$N^1$ is a nucleoside derivative radical of the formula II or IV, and
$N^2$ is a nucleoside derivative radical of the formula III, in which, in each case,
$R^1$ is hydroxyl;

$R^2$ to $R^7$ are hydrogen; and
$R^8$ is an oxygen atom by way of which the $N^1$ or $N^2$ is linked to the glycerol-1,3-diphosphate backbone of the formula I.
g) Compounds of the formula I according to group c), in which, in particular,
$N^1$ and $N^2$ are a nucleoside derivative radical of the formula IV,
in which, in $N^1$,
$R^1$ is an amino, palmitoylamino or octadecylamino group;
$R^2$, $R^5$ and $R^7$ are hydrogen;
$R^3$, $R^4$ and $R^8$ are identical or different and are hydrogen, hydroxyl or fluorine;
and in which, in $N^2$,
$R^1$ is a hydroxyl group;
$R^2$ is methyl or halogen;
$R^3$, $R^4$, $R^5$ and $R^7$ are hydrogen, where two vicinal radicals thereof are optionally dispensed with if a double bond is present in position a;
$R^6$ is hydrogen, fluorine, azido or hydroxyl; and
$R^8$ in $N^1$ and $N^2$ is in each case an oxygen atom by way of which the $N^1$ and $N^2$ are linked to the glycerol-1,3-diphosphate backbone.
h) Compounds of the formula I according to group G, in which, in particular, in $N^1$ and $N^2$,
$R^1$ is identical or different and is a hydroxyl group or an amino group;
$R^2$ is identical or different and is hydrogen or methyl;
$R^4$, $R^5$ and $R^7$ are hydrogen;
$R^6$ is azido in $N^1$ and fluorine in $N^2$; and
$R^8$ is the oxygen atom by way of which the $N^1$ and $N^2$ are linked to the glycerol-1,3-diphosphate backbone.
i) Compounds of the formula I according to group g), in which, in particular, in $N^1$,
$R^1$ is an amino or palmitoylamino group,
$R^2$ and $R^7$ are hydrogen;
$R^3$ and $R^4$ are fluorine, hydrogen or hydroxyl,
$R^5$ is hydrogen or an ethynyl radical,
$R^6$ is hydroxyl, and
in which, in $N^2$,
$R^1$ is hydroxyl,
$R^2$ is fluorine,
$R^3$, $R^4$, $R^5$ and $R^7$ are hydrogen;
$R^6$ is hydroxyl, and
$R^8$ in $N^1$ and $N^2$ is in each case an oxygen atom by way of which $N^1$ and
$N^2$ are linked to the glycerol-1,3-diphosphate backbone.

The novel, preferably amphiphilic, glyceryl nucleotides of the formula Ia can be prepared by a compound of the formula Ib

in which
one of the radicals $A^{1B}$, $A^{2B}$ and $A^{3B}$ is a hydroxyl, mercapto, hydrogen phosphonate or thiohydrogen phosphonate group, and the other two radicals possess the meanings given above for $A^1$, $A^2$ and $A^3$, where at least one of the two radicals is a nucleoside group in accordance with the above definition, a) being condensed, in the presence of an acid chloride, with a nucleoside or nucleoside derivative in accordance with the abovementioned definition, where the nucleoside derivative additionally carries a hydrogen phosphonate or thiohydrogen phosphonate group if one of the radicals $A^{1B}$, $A^{2B}$ and $A^{3B}$ is a hydroxyl group or a mercapto group; and the resulting product being oxidized; or
b) being reacted with (ethoxycarbonyl)dichlorophosphonate and the acid chloride and ethoxy groups subsequently being hydrolyzed under alkaline conditions.

The novel, preferably amphiphilic, glyceryl nucleotides of the formula I, in which $N^1$ and $N^2$ are a D- or L-configured nucleoside derivative, can be prepared by a compound of the formula V

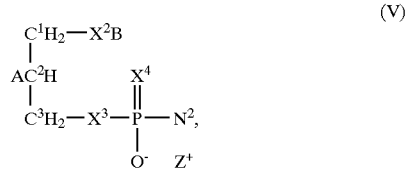

in which the radicals A, XB and the phosphoric acid radical can be linked in any arbitrary sequence to the $C^1$-, $C^2$- and $C^3$ atoms of the glycerol backbone; the radicals A, $X^2$, $X^3$, $X^4$, $N^2$ and Z have the given meanings; and $X^2B$ is a hydroxyl, thiol, hydrogen phosphonate or thiohydrogen phosphonate group;

being condensed with a nucleoside derivative of the above formula II, III or IV, in which the radicals $R^1$ to $R^8$ have the given meanings, and, in addition, $R^8$ can also be 4-mono-, 4,4'-dimethoxytriphenylmethoxy, hydrogen phosphonate or thiohydrogen phosphonate; $R^3$, $R^4$, $R^5$ and $R^6$ can additionally be a linear or branched carboxyl radical which possesses 1–24 C atoms and which can be substituted by a phenyl radical; and one of the radicals $R^3$, $R^4$, $R^5$, $R^6$ and $R^8$ is always hydrogen phosphonate or thiohydrogen phosphonate if, in a compound of the formula V, $X^2B$ is hydroxyl or thiol, but, on the other hand, none of these radicals is hydrogen phosphonate or thiohydrogen phosphonate if $X^2B$ is hydrogen phosphonate or thiohydrogen phosphonate; in the presence of an acid chloride, and subsequently oxidized.

The condensation takes place particularly satisfactorily in the presence of acid anhydrides or acid halides, such as, in particular, pivaloyl chloride, at from −80° C. to +100° C., for example at about 0–20° C. The oxidation takes place particularly satisfactorily at from −80° C. to +100° C., for example at about 0–20° C., with a) the P—H bond being oxidized to a P=O bond with iodine in aqueous organic solvents, or b) the P—H bond being oxidized to a P=S bond with $S_8$ in triethylamine/$CS_2$.

After oxidizing and working up chromatographically, the 4-mono- or 4,4'-dimethoxytriphenylmethyl group is replaced with hydroxyl. If required, acyl radicals are converted hydrolytically into mercapto, hydroxyl and/or amino groups.

The novel, preferably amphiphilic, compounds of the formula 1, in which $N^1$ is a hydroxycarbonyl radical which is bonded in its acid or salt form, can be prepared by reacting a compound of the formula V, in which B is hydrogen, with (ethoxycarbonyl) phosphoryl dichloride in a manner known per se. The reaction takes place particularly successfully in mixtures with halogenated hydrocarbons, such as, in particular, pyridine/chloroform, acetonitrile/chloroform or pyridine/methylene chloride and acetonitrile/methylene chloride, and trimethyl phosphate at from −10° C. to +80°

C., for example at about 0–10° C. After reacting and working up chromatographically, the acid chloride group and the ethoxy group are changed into hydroxyl groups or corresponding salt forms by subsequent hydrolysis under alkaline conditions (J. Med. Chem. (1986) 29, 1389).

The compounds of the formula V which are used as starting material can be prepared by condensation of a compound of the formula VI

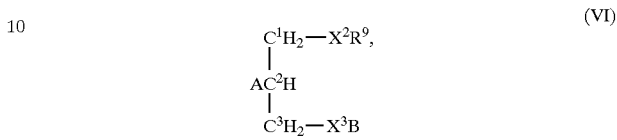

in which the radicals
A, $X^2R^9$ and $X^3B$ can be linked in any arbitrary sequence to the $C^1$, $C^2$ and $C^3$ atoms of the glycerol backbone;
A and $X^2$ have the abovementioned meanings;
$R^9$ is 4-mono- or 4,4'-dimethoxytriphenylmethyl or a linear or branched acyl radical which possesses 1–24 C atoms and which can be substituted by an aromatic radical; the radical $X^3B$ is a hydroxyl, thiol, hydrogen phosphonate orthiohydrogen phosphonate group;
with a nucleoside derivative of the formula II, III or IV, in which the radicals $R^1$–$R^8$ have the abovementioned meanings,
where one of the radicals $R^3$, $R^4$, $R^5$, $R^6$ and $R^8$ is also always hydrogen phosphonate or thiohydrogen phosphonate if, in a compound of the formula VI, the radical $X^3B$ is hydroxyl or thiol, but, on the other hand, none of the radicals is hydrogen phosphonate or thiohydrogen phosphonate if, in a compound of the formula VI, $X^3B$ is hydrogen phosphonate or thiohydrogen phosphonate;
in the presence of an acid chloride and subsequently oxidizing with iodine or sulfur in a manner known per se (Tetrahedron Lett., (1986) 27, 469; ibid. 5575).

After the chromatographic working up, the 4-mono- or 4',4'-dimethoxytriphenylmethyl radical is replaced with hydrogen under acid conditions, while the acyl radical is replaced with hydrogen under alkaline conditions.

The starting materials which are required for the reactions are known substances or can be prepared in analogy with known methods (Hel. Chim. Acta (1982) 65, 1059; Liebigs Ann. Chem. (1991) 765; ibid. (1996) 365; Antivir. Chem & Chemother. (1998) 9, 33. J. C. S. Perkin 1 (1982) 11 71; Makromol. Chem. (1986) 187,809; Tetrahedron Left. (1986) 27, 2661).

The compounds according to the invention can have an amphiphilic character or a non-amphiphilic character. However, amphiphilic compounds are particularly preferred.

The conversion, according to the invention, of Foscarnet and the therapeutically active nucleoside analogs into amphiphilic glyceryl nucleotides brings about a marked alteration in pharmokinetic behavior. As a result, the dose to be administered can be surprisingly increased in comparison with that of the respective monomer without this, at the same time, leading to any amplification of all the toxic side effects of these highly potent drugs. In addition, amphiphilic glyceryl nucleotides still have an effect even in the presence of resistance to the respective monomeric nucleoside analogs.

The amphiphilic character of the amphiphilic glyceryl nucleotides according to the invention makes it possible to implement a variety of administration schemes. The lipophilic region of the glyceryl nucleotides results in the active compounds being stably incorporated into liposomes together with matrix lipids, promotes the cell uptake of the amphiphilic glyceryl nucleotides which are dissolved in water, and at the same Ume protects them from an enzymic hydrolysis which is too rapid. The hydrophilic region enables the active compounds to be water-soluble as well, presumably by way of micelle formation. The advantage of the alternative possibility of administering the amphiphilic glyceryl nucleotides is that the desired slow-release effect of the dimers is achieved in aqueous solutions as well as in a liposome dispersion, which means that there is no need to rely exclusively on liposome technology but that this technology can be used if required, something which is in turn not readily possible in the case of active compounds which are only soluble in water.

Another advantage of the amphiphilic glyceryl nucleotides according to the invention is that they can be incorporated into liposomes together with differing quantities of one or more other active compounds, with this resulting in synergistic effects. Using these amphiphilic glyceryl nucleotides, and/or in a composition together with a biologically tolerated excipient, and/or using remedies which comprise the compounds according to the invention at least in one or more of the compositions, it is possible to optimize the therapy of cancer diseases and infectious diseases caused by viruses.

In general, the compounds according to the invention are employed in the form of pharmaceutical remedies for treating an individual, preferably a mammal, in particular a human. Thus, the compounds are usually administered in the form of pharmaceutical compositions which comprise a pharmaceutically tolerated excipient together with at least one nucleoside phosphate analog according to the invention, where appropriate a mixture of several compounds according to the invention as well as, and, where appropriate, additional active compounds which can be used for the particular therapeutic effect which is desired. These compositions can be administered, for example, orally, rectally, transdermally, subcutaneously, intravenously, intramuscularly or intranasally.

Examples of suitable pharmaceutical formulations are solid medicinal forms, such as powders, granules, tablets, lozenges, sachets, cachets, sugar-coated tablets, capsules, such as hard and soft gelatin capsules, suppositories or vaginal medicinal forms; semisolid medicinal forms, such as ointments, cremes, hydrogels, pastes or plasters, and also liquid medicinal forms, such as solutions, emulsions, in particular oil-in-water emulsions, suspensions, for example lotions, injection and infusion preparations and eye and ear drops. Implanted slow-release devices can also be used for administering compounds according to the invention. It is furthermore possible to use liposomes, microspheres or polymer matrices as well.

Compounds according to the invention are usually mixed or diluted with an excipient when preparing the compositions. Excipients can be solid, semisolid or liquid materials which serve as a vehicle, carrier or medium for the active compound.

Suitable excipients include, for example, lactose, glucose, sucrose, sorbitol, mannitol, starches, gum arabic, calcium phosphate, alginates, tragacanth, gelatin, calcium silicate, microcrystalline cellulose, polyvinylpyrrolidone, cellulose, water, syrup and methyl cellulose. In addition, the formulations can comprise pharmaceutically acceptable carriers or customary auxiliary substances, such as lubricants, for example talc, magnesium stearate and mineral oil; wetting agents; emulsifying and suspending agents; preservatives, such as methyl- and propylhydroxybenzoates; antioxidants; antiirritants; chelating agents; coating auxiliaries; emulsion stabilizers; film formers; gel formers; odor masking agents; taste corrigents; resins; hydrocolloids; solvents; solubilizing agents; neutralizing agents; permeation accelerators, pigments; quatemary ammonium compounds; regreasing and hypergreasing agents; ointment, cream or oil bases; silicone derivatives; spreading auxiliaries; stabilizers, sterilizing agents; suppository bases, tablet auxiliaries, such as binders, fillers, lubricants, disintegrants or coatings; propellants; desiccants, opacifiers; thickeners; waxes; emollients; white mineral oils. A formulation in this regard is based on specialist knowledge, as presented, for example, in H. P., Lexikon der Hilfsstoffe für Pharmazie, Kosmetik und angrenzende Gebiete, (Encyclopedia of auxiliary substances for pharmacy, cosmetics and related areas), 4th edition, Aulendorf: ECV-Edition-Kantor publishing company, 1996.

A variety of compositions are prepared in order to ensure that the compounds according to the invention are administered as effectively as possible. A feature common to all these compositions is that the compounds according to the invention are combined with an organic carrier.

A preferred embodiment of these compositions provides for the association of the compoundsaccording to the invention in the form of unilamellar to oligolamellar liposomes having a diameter of at most 0.4 μm All the methods which are known per se for preparing liposomes, such as ultrasound, gel chromatography, detergent dialyse and high pressure filtration, can be used for forming the liposomes. The lipophilic radicals which are in each case introduced have an important influence on the size and stability of the liposomes, which are formed from the respective glyceryl nucleotides together with additional lipid components (cf. Liposomes: Physical Structure to Therapeutic Applications in: Research monographs in cell and tissue physiology vol. 7, G. G. Knight editor, Elsevier (1981) as well).

Another preferred possibility of combining the compounds according to the invention with an organic carrier is that of enclosing the compounds in biologically tolerated nanoparticles. Nanoparticles is the name given to organochemical polymers to which the compounds according to the invention are added during the polymerization, such that these compounds are efficiently enclosed in the nanoparticles (cf. Bender et al., Antimicrobial agents and Chemotherapy (1996), 40 (6) 1467–1471).

In a preferred embodiment, the composition is effected using components which become specifically concentrated in the cells and/or organs to be treated. In this connection, the composition of the liposomes can, for example, be selected such that the liposomes are additionally provided with molecules, such as antibodies, charged lipids or lipids which are modified with hydrophilic head groups, so that the composition becomes preferentially concentrated in the cells and/or organs to be treated. Such a composition, containing molecules which are specifically directed against tumor cells, virus-infected cells and/or organs, increases the therapeutic effect of the drugs and at the same time reduces the toxicity for uninfected tissues.

The compositions can be processed to give a remedy which, in addition to the compounds according to the invention and, where appropriate, the organic carrier, also comprises customary excipients and/or diluents and/or auxiliary substances. Examples of customary excipients are mannitol, glucose, albumins or the like, while physiological sodium chloride solutions or a 5% glucose solution is in the main used as the diluent. Furthermore, it is customary to buffer the solutions with suitable reagents, for example phosphates. In addition to this, it is possible to add all the other agents which are customary for preparing pharmaceutical remedies, provided they do not attack the composition consisting of the organic carrier and the compounds according to the invention. The remedy can be administered either as an infusion solution or else orally.

However, the conversion into amphiphilic glyceryl nucleotides does not only have the effects of increasing the resistance to enzymic hydrolysis and significantly widening the possible administration forms; it also surprisingly optimizes cytostatic and virustatic effects.

The amphiphilic glyceryl nucleotides can be employed against malignant diseases of the hematopoietic cells and solid tumors. As a result of the superior cytostatic effect, there are far fewer serious side effects. It is possible to employ higher doses of the cytostatically active compounds according to the invention and therapy can be carried out in chronological intervals.

Surprisingly, the nucleoside phosphate analogs according to the invention also exhibit virustatic effects such that they can be used in the chemotherapy of viral infections and for overcoming drug resistances, as, for example, in the case of herpes, hepatitis and AIDS.

The invention therefore also relates to the use of compounds according to the invention for treating cancer diseases, such as leukemia, lung cancer, intestinal cancer, cancer of the central nervous system, melanomas, ovarian cancer, kidney cancer, prostate cancer and breast cancer; and also for treating viral diseases, such as AIDS, hepatitis A, B and C and herpes.

The following examples explain the invention without, however, restricting it to these examples.

EXAMPLE 1

Preparing 3'-azido-2',3'-dideoxythymidylyl-(5'→2)-1-O-octadeyl-rac-glycerol-3-(hydroxycarbonyl)phosphonate a) Preparing the Starting Material 2.5 g (3.8 mmol) of 3-O-(4-monomethoxytrityl)-1-O-octadecyl-rac-glycerol-2-hydrogen phosphonate are dissolved, together with 1 g (3.8 mmol) of 3'-azido-2',3'-dideoxythymidine, in 15 ml of anhydrous pyridine. 2.3 ml (19 mmol) of pivaloyl chloride are added, with the exclusion of moisture, to the solution, which has been cooled down to approx. 10° C., and the whole is stirred at room temperature for 7 min. 1 ml of water and 20 ml of a 0.2 M solution of iodine in THF are then added, one after the other, to the reaction mixture, which has been cooled down to 0° C. and which is subsequently stirred for 1 h without cooling. Excess iodine is reduced by adding solid sodium hydrogen sulfite before the reaction mixture is concentrated in a rotary evaporator down to a syrup, which is taken up in 80 ml of dichloromethane; this mixture is then shaken out three times against 50 ml of water/methanol 1:1; V:V. The organic phase is concentrated down in a rotary evaporator to a syrup, which is coevaporated a further three times with toluene. In order to replace the 4-monomethoxytrityl group with hydrogen, the syrup is dissolved in 50 ml of acetic acid/water; 4:1; V:V, after which this solubon is heated at 40° C. for 5 min and then once again concentrated in a rotary evaporator down to a syrup; the syrup is then coevaporated twice again with toluene, then dissolved in 25 ml of chloroform/methanol; 98:2; V:V and fractionated on a silica gel column using a chloroform/methanol gradient. The product-containing fractions are converted in a rotary evaporator into 2 g (3 mmol) of a foam, which exhibits an $R_f$ value of 0.48 in the solvent system chloroform/methanol; 7:3; V:V.

b) Preparing the Final Product

The foam obtained as described in a) is added in portions, while stirring, to a solution, which has been cooled down to 0° C., of 1 g of ethoxycarbonyl phosphonyl dichloride dissolved in 12 ml of trimethyl phosphate. The reaction mixture is stirred at 0° C. for a further 4 h, after which 50 ml of ether and 50 ml of water are added, while cooling, and the whole is shaken thoroughly. The aqueous phase is separated off and the organic phase is extracted once again by shaking with water. The combined aqueous phases are neutralized with 2 M sodium hydroxide solution, while cooling with ice, and are then concentrated down into a syrup, which is taken up in ether and crystallized while ultrasonicating. The resulting precipitate is centrifuged off, dried and dissolved in 10 ml of water; 10 ml of 2 M sodium hydroxide solution are then added and this reaction solution is stirred at room temperature for 1 h. It is then neutralized with 2 N hydrochloric acid, concentrated in vacuo and desalted on a Sephadex Glo column. The product-containing fractions are lyophilized and yield 2.1 g of 3'-azido-2',3'-dideoxythymidylyl-(5'→2)-1-O-octadeyl-rac-glycerol-3-(hydroxycarbonyl)-hydrogen phosphonate in the form of a colorless powder, which exhibits an $R_f$ value of 0.1 on a silica gel thin layer chromatography plate in the solvent system chloroform/methanol; 6:4; V:V. The calculated molecular mass (769.77) is confirmed by the molecule peak (768.5) in an ion spray mass spectrum.

EXAMPLE 2

Preparing arabinocytidylyl-(5'→1)-2-O-octadecyl-rac-glycerylyl-(3→5')-5-fluoro-2'-deoxyuridine a) Preparing the Starting Material 4.8 g (7 mmol) of 1-O-(4-monomethoxytrityl)-2-O-octadecyl-rac-glycerol-3-hydrogen phosphonate are condensed together with 2 g (7 mmol) of 3'-O-acetyl-5-fluoro-2'-deoxyuridine in 50 ml of anhydrous pyridine in the added presence of 4.3 ml of pivaloylchloride, in analogy with a) from Example 1, and oxidized with 32 ml of a 0.2 M solution of iodine in THF. For replacing the 4-monomethoxytrityl group with hydrogen, the syrup which is obtained after condensation is dissolved in 70 ml of acetic acid/water; 4:1; v:v and this solution is heated under reflux for 30 min. The cooled solution is concentrated in a rotary evaporator down to a syrup, which is coevaporated twice with toluene and then taken up in 35 ml of dichloromethane/methanol; 9:1: V:V; this mixture is then fractionated on a silica gel column using a dichloromethane/methanol gradient. The product-containing fractions are converted in vacuo into 3.0 g of foam, which exhibits an $R_f$ value of 0.32 on a silica gel thin layer chromatography plate in the solvent system chloroform/methanol; 7:3; V:V.

b) Preparing the Final Product

The foam obtained as described in a) and 2.8 g (4.3 mmol) of 2',3'-di-O-acetyl-$N^4$-stearoylarabinocytidine-5'-hydrogen phosphonate are condensed in 35 ml of anhydrous pyridine, in the added presence of 3 ml of pivaloyl chloride, in analogy with a) from Example 1. After 2 ml of water has been added, oxidation is carried out by adding 20 ml of an 0.2 M solution of iodine in THF. After having been concentrated in a rotary evaporator, the reaction mixture is taken up in dichloromethane and this solution is extracted three times with a solution comprising saturated aqueous NaCl/water/methanol; 1:1:2; V:V:V, The organic phase is concentrated in vacuo down to a syrup, which is then coevaporated three times with toluene. The syrup is then taken up in dichloromethane/methanol; 9:1; V:V and fractionated on a silica gel column using a dichloromethane/methanol gradient. The product-containing fractions are concentrated in vacuo down to a syrup, which, having been dissolved in hot ethyl acetate, crystallizes at 0° C. In order to replace the acyl protecting groups with hydrogen, the precipitate is dissolved in a little dichloromethane/methanol; 1:1; V:V. Methanol which has been saturated with ammonia at room temperature is added to the solution, which is left to stand sealed, at room temperature, for 36 h, after which it is concentrated down in a rotary evaporator until crystallization sets in. The arabinocytidylyl-(5'→1)-2-O-octadecyl-rac-glycerylyl-(3→5')-5-fluoro-2'-deoxyuridine which has precipitated out after 12 h of standing at 0° C. is filtered off with suction and washed with ether and, after drying, yields 2.3 g of a white powder, which exhibits an $R_f$ value of 0.10 on a silica gel thin layer chromatography plate in the solvent system chloroform/methanol/$NH_3$ 10:10:3; V:V:V. The calculated molecular mass (957.93) is confirmed by the molecule peak (957.0) in an ion spray mass spectrum.

EXAMPLE 3

Preparing $N^4$-palmitoyl-3'-thia-2',3'-dideoxycytidylyl-(5'→1)-2-O-octadecyl-rac-glycerylyl-(3→5')-3'-azido-2',3'-dideoxythymidine a) Preparing the Starting Material:

2.4 g (5.3 mmol) of 1-O-acetyl-2-O-octadecyl-rac-glycerol-3-hydrogen phosphonate and 1.4 g (5.3 mmol) of 3'-azido-2',3'-dideoxythymidine are condensed, in analogy with a) from Example 1, in 30 ml of anhydrous pyridine in the added presence of 3.5 ml (28.4 mmol) of pivaloyl chloride. After 2 ml of water have been added, oxidation is carried out using 25 ml of a 0.2 M solution of iodine in THF. The reaction mixture is concentrated in a rotary evaporator and taken up in 85 ml of chloroform; this solution is then extracted by shaking three times with in each case 40 ml of a solution comprising saturated aqueous NaCl/water/methanol; 1:1:2; V:V:V. The organic phase is then concentrated down to a syrup, which, for the purpose of replacing the acetyl group with hydrogen, is treated for 12 h with methanol which has been saturated with ammonia at room temperature. After the concentration in vacuo which follows, the syrup is taken up in dichloromethane and fractionated on a silica gel column using a dichloromethane/methanol gradient. The product-containing fractions are concentrated in vacuo down to a syrup, which is dissolved in ethanol and which, forms 3.0 g of colorless crystals at −25° C.; these crystals exhibit an $R_f$ value of 0.26 in the solvent system chloroform/methanol; 7:3; V:V.

b) Preparing the Final Product

The crystals which are obtained as described in a) and 2.4 g (4.5 mmol) of $N^4$-palmitoyl-3'-thia-2',3'-dideoxycytidine-5'-hydrogen phosphonate are condensed, in analogy with a) from Example 1, in 40 ml of dry pyridine in the added presence of 3.0 ml of pivaloyl chloride, and oxidation is then carried out using 20 ml of a 0.2 M solution of iodine in THF. The resulting syrup is dissolved in 100 ml of chloroform/methanol; 9:1; V:V and fractionated on a silica gel column using a chloroform/methanol gradient. The product-containing fractions are concentrated in vacuo down to a syrup from which, after adding methanol, 2.5 g of $N^4$-palmitoyl-3'-thia-2',3'-dideoxycytidylyl-(5'→1)-2-O-octadecyl-glycerylyl-(3→5')-3'-azido-2',3'-dideoxythymidine crystallize out in the form of a white powder, which exhibits an $R_f$ value of 0.20 on a silica gel thin layer chromatography plate in the solvent system chloroform/methanol; 7:3; V:V. The calculated molecular mass (1203.5) is confirmed by the molecule peak (1202.5) in an ion spray mass spectrum.

EXAMPLE 4

Preparing 3'-azido-2',3'-dideoxythymidylyl-(5'→1)-2-O-octadecyl-racglycerylyl-(3→5')-$N^4$-palmitoyl-2',3'-dideoxycytidine Preparing the Final Product The crystals obtained as described in a) from Example 3 and 2.3 g (4.5 mmol) of $N^4$-palmitoyl-2',3'-dideoxycytidine-5'-hydrogen phosphonate are condensed, in analogy with a) from Example 1, in 40 ml of anhydrous pyridine in the added presence of 3.0 ml (24.4 mmol) of pivaloyl chloride, and oxidized with 20 ml of a 0.2 M solution of iodine in THF. The syrup obtained after the condensation is dissolved in 130 ml of hot ethanol and this solution is filtered; 5.1 g of 3'-azido-2',3'-dideoxythymidylyl-(5'→1)-2-O-octadecyl-rac-glycerylyl-(3→5')-$N^4$-palmitoyl-2',3'-dideoxycytidine then crystallize out, at −25° C., in the form of colorless crystals which exhibit an R. value of 0.26 on a silica gel plate in the solvent system chloroform/methanol; 6:4; V:V. The calculated molecular mass (1185.40) is confirmed by the molecule peak (1184.0) in an ion spray mass spectrum.

EXAMPLE 5

Preparing $N^4$-palmitoyl-2',3'-dideoxycytidylyl-(5'→1)-2-O-palmitoyl-rac-glycerylyl-(3→5')-3'-azido-2',3'-dideoxythymidine a) Preparing the Starting Material 3.2 g (7.2 mmol) of 1-O-acetyl-2-O-palmitoyl-racglycerol-3-hydrogen phosphonate and 2.0 g (7.2 mmol) of 3'-azido-2',3'-dideoxythymidine are condensed, in analogy with a) from Example 1, in 60 ml of dry pyridine in the added presence of 4.5 ml (36.6 mmol) of pivaloyl chloride and oxidized with 32 ml of a 0.2 M solution of iodine in THF. The syrup obtained after the condensation is taken up in 75 ml of chloroform/methanol; 9:1; V:V and fractionated on a silica gel column using a chloroform/methanol gradient. The product-containing fractions are concentrated in vacuo and the residue is taken up in 15 ml of chloroform; 120 ml of methanol which has been saturated with ammonia at room temperature is then added and the mixture is left to stand at room temperature for 90 min. The reaction mixture is then concentrated in vacuo and the residue is coevaporated with toluene to dryness. The residue is taken up in chloroform/methanol; 9:1; V:V and fractionated on a silica gel column using a chloroform/methanol gradient. The product-containing fractions are concentrated in vacuo down to 2.7 g of a foam which exhibits an $R_f$ value of 0.24 in the solvent system chloroform/methanol; 7:3; V:V.

b) Preparing the Final Product

The foam obtained as described in a) and 2.1 g (4.1 mmol) of $N^4$-palmitoyl-2',3'-dideoxycytidine-5'-hydrogen phosphonate are condensed, in analogy with a) from Example 1, in 35 ml of dry pyridine in the added presence of 25 ml (20.3 mmol) of pivaloyl chloride and oxidized with 20 ml of a 0.2 M solution of iodine in THF. The syrup which is obtained after condensation is taken up in 50 ml of chloroform/methanol; 95:5; V:V and fractionated on a silica gel column using a chloroform/methanol gradient. The product-containing fractions are concentrated in vacuo down to a syrup from which, on adding methanol, 2.3 g of $N^4$-palmitoyl-2',3'-dideoxycytidylyl-(5'→1)-2-O-palmitoyl-rac-glycerylyl-(3→5')-3'-azido-2',3'-dideoxythymidine crystallize out in the form of a white powder which exhibits an $R_f$ value of 0.25 on a silica gel thin layer chromatography plate in the solvent system chloroform/methanol; 6:4; V:V. The calculated molecular mass (1171.32) is confirmed by the molecule peak (1170.0) in an ion spray mass spectrum.

EXAMPLE 6

Preparing 3'-azido-2',3'-dideoxythymidylyl-(5'→1)-2-O-octadecyl-rac-glycerylyl-(3→5')-2',3'-dideoxyinosine a) Preparing the Starting Material The starting material obtained as described in a) from Example 3 is dissolved in a mixture comprising 10 ml of dry pyridine and 40 ml of dry dioxane, after which 1.1 g (5.3 mmol) of salicyl chlorophosphite are added and the mixture is shaken at room temperature for 1 h. The reaction mixture is then cooled down to 0° C., after which 2 ml of water are added and the mixture is shaken at room temperature for a further 15 min and concentrated in vacuo down to a syrup; the syrup is taken up in 120 ml of water and this solution is extracted by shaking three times with 40 ml of ethyl acetate on each occasion. The aqueous phase is concentrated in vacuo and lyophilized. 2.5 g of a white powder are obtained, with this powder exhibiting an $R_f$ value of 0.15 on a silica gel plate in the solvent system chloroform/methanol; 7:3; V:V.

b) Preparing the Final Product

The lyophilizate obtained as described in a) is condensed, in analogy with a) from Example 1, with 0.8 g (3.4 mmol) of 2',3'-dideoxyinosine in 25 ml of pyridine in the added presence of 2.0 ml (16.3 mmol) of pivaloyl chloride and oxidized with 16 ml of a 0.2 M solution of iodine in THF. The syrup obtained after the condensation is taken up in 50 ml of chloroform/methanol; 9:1; V:V and fractionated on a silica gel column using a chloroform/methanol gradient. The product-containing fractions are concentrated in vacuo down to a syrup from which, on adding ether, 1.1 g of 3'-azido-2',3'-dideoxythymidylyl-(5'→1)-2-O-octadecyl-rac-glycerylyl-(3→5')-2',3'-dideoxyinosine crystallize out in the form of white crystals which exhibit an $R_f$ value of 0.21 on a silica gel plate in the solvent system chloroform/methanol; 1:1; V:V. The calculated molecular mass (971.99) is confirmed by the molecule peak (970.5) in an ion spray mass spectrum.

EXAMPLE 7

Preparing 3'-fluoro-2',3'-dideoxythymidylyl-(5'→1)-2-O-octadecyl-rac-glycerylyl-(3→5')-3'-azido-2',3'-dideoxythymidine a) Preparing the Starting Material 4.3 g (9.5 mmol) of 1-O-acetyl-2-O-octadecyl-racglycerol-3-hydrogen phosphonate are condensed, in analogy with a) from Example 1, together with 2.3 g (9.5 mmol) of 3'-fluoro-2',3'-dideoxythymidine in 25 ml of pyridine in the added presence of 5.7 ml of pivaloyl chloride and oxidized with 45 ml of a 0.2 M solution of iodine in THF. The syrup obtained after the condensation is taken up in a little chloroform, after which 200 ml of methanol, which has been saturated with ammoniak at room temperature, are added; the mixture is shaken vigorously and then left overnight at room temperature. The reaction mixture is then concentrated in vacuo until crystallization sets in. The precipitate which is obtained after 12 h of standing at −25° C. is filtered off with suction and dried. This results in 3.4 g of a white powder which exhibits an $R_f$ value of 0.71 on a silica gel thin layer chromatography plate in the solvent system chloroform/methanol; 6:4; V:V.

b) Preparing the Final Product 3.4 g (5.2 mmol) of the powder obtained as described in a) and 1.7 g (2.3 mmol) of 3'-azido-2',3'-dideoxythymidine-5'-hydrogen phosphonate are condensed, in analogy with a) from Example 1, in 45 ml of dry pyridine in the added presence of 3.5 ml of pivaloyl chloride and oxidized with 25 ml of a 0.2 M solution of iodine in THF. The syrup obtained after the condensation is dissolved in 100 ml of chloroform/methanol; 9:1; V:V and fractionated on a silica gel column using a chloroform/methanol gradient. The product-containing fractions are concentrated in vacuo down to a syrup from which, on adding methanol, 2.7 g of 3'-fluoro-2',3'-dideoxythymidylyl-(5'→1)-2-O-octadecyl-rac-glycerylyl-(3→5')-3'-azido-2',3'-dideoxythymidine are obtained in the form of white crystals which exhibit an $R_f$ value of 0.45 on a silica gel thin layer chromatography plate in the solvent system chloroform/methanol; 6:4; V:V. The calculated molecular mass (979.91) is confirmed by the molecule peak (979.0) in an ion spray mass spectrum.

EXAMPLE 8

Preparing a Composition which Comprises an Organic Carrier, One of the Amphiphilic Glyceryl Nucleotides According to the Invention and Cholesterol.

1. Assembling the Liposomes

Liposomes containing 10 mg of the compound according to the invention per ml. 1 ml of liposomes contain: 100 mg of phosphatidylcholine, 10 mg of chlolesterol and 10 mg of the compound according to the invention dispersed in 0.9% sodium chloride solution which, if necessary, is adjusted to a desired pH, for example using phosphate buffer. Instead of using the sodium chloride solution, which is buffered where appropriate, it is also possible to use a 67 nM physiological phosphate buffer or a 5% glucose solution.

2. Producing the Liposome Preparations by Means of Ultrasonication

Preparing a 2.5 ml liposome dispersion which contains 10 mg of the compound according to the invention per ml. 250 mg of soybean phosphatidyl choline are dissolved, in a 100 ml round bottom flask, in 5 ml of tert-butanol; 25 mg of cholesterol are then added, with the cholesterol dissolving when the mixture is warmed (50° C.). 25 mg of the compound according to the invention, which are dissolved in the appropriate quantity of DMSO (0.25 ml–1 ml), are added to this solution and the resulting solution is concentrated down to half the volume in a rotary evaporator and then lyophilized. 2.5 ml of water are added to the resulting lyophilizate, which is then converted into a suspension by means of ultrasonication and subsequently lyophilized once again. The lyophilizate is suspended in 2.5 ml of a 0.9% NaCl solution and sonicated, while cooling, in a thick-walled glass centrifuge tube for 1 h using the ultrasonication tip (3 mm) of a Branson 250 sonifier. This results in an opalescent liposome dispersion having the composition 100 mg of SPC, 10 mg of cholesterol and 10 mg of the compound according to the invention per ml.

EXAMPLE 9

In-vitro Investigation of the Anti-HIV Effect of a Compound According to the Invention The in vitro virusstatic (anti-HIV) effect of the novel compound $N^4$-palmitoyl-2',3'-dideoxycytidylyl-(5'→1)-2-O-palmitoyl-rac-glycerylyl-(3→5')-3'-azido-2',3'-dideoxythymidine (NSC 704532-F/1) can be demonstrated in the following experimental arrangement. T4 lymphocytes (cell line: CEM-SS), which are killed by HIV within two replication cycles, are used as the test system. That which is detected is the inhibition of cell death. The compound according to the invention is dissolved in DMSO and this solution is diluted with cell culture medium in the ratio 1:100. Semilogarithmic (($log_{10}$) dilutions are then prepared. T4 lymphocytes and, after a given period of time, HI viruses, are then added to these solutions. This results in a dilution of at least 1:200 based on the original solution of the compound according to the invention in DMSO. Uninfected T4 lymphocytes, which are only incubated with the compound according to the invention, serve as the toxicity control. Infected and uninfected T4 cells in the absence of compound according to the invention serve as additional standard controls. The cell cultures are incubated for 6 days at 37° C. in a 5% $CO_2$ atmosphere, after which tetrazolium salt (XTT) is added to all the cell cultures and the formazan color reaction then appears in the viable cells. All the cell cultures are examined spectrophotometrically in order to quantify production of formazan. In addition to this, individual cultures are examined microscopically in order to confirm the anti-HIV activity. The virus-infected cells which have been treated with the compound according to the invention are compared with the standard on the same plate. The in-vitro anti-HIV activity data, which were determined within the context of a National Cancer Institute Developmental Therapeutics Program, are summarized in the following table. It follows from the data that 50% cell growth ($IC_{50}$) occurs at $>1.00\times10^{-6}$ mol of the compound according to the invention, while 50% protection from infection ($EC_5$.) is at $1.79\times10^{-8}$ mol, and the therapeutic span $TI_{50}$ (IC/EC) is at $>5.59\times10^{+1}$.

TABLE

Test results for the anti-HIV activity of
$N^4$-palmitoyl-2',3'-dideoxycytidylyl-(5' → 1)-2-O-palmitoyl-rac-glycerylyl-(3 → 5')-3'-azido-2',3'-dideoxythymidine

| Dose | Percent | Percent of control | |
|---|---|---|---|
| (molar) | protection | infected | uninfected |
| 3.17 * 10$^{-10}$ | 1.88 | 5.80 | 105.43 |
| 1.00 * 10$^{-9}$ | 0.22 | 4.21 | 105.03 |
| 3.17 * 10$^{-9}$ | 10.68 | 14.25 | 101.22 |
| 1.00 * 10$^{-8}$ | 20.44 | 23.62 | 99.64 |
| 3.16 * 10$^{-8}$ | 79.40 | 80.22 | 104.96 |
| 1.00 * 10$^{-7}$ | 106.32 | 106.07 | 112.26 |
| 3.16 * 10$^{-7}$ | 104.33 | 104.16 | 112.02 |
| 1.00 * 10$^{-6}$ | 114.05 | 113.49 | 119.96 |

EXAMPLE 10

In vitro Cytostatic Effect of Compounds According to the Invention.

a) Experimental Arrangement

Tumor cell lines, the 50% inhibition (GI50) and 100% inhibition (TGI) of the growth of which by the compound according to the invention are determined at various concentrations, are used as a test system. The toxicity ($LC_{50}$) of the compound on these cells is also determined. A series of microtiter plates is inoculated with the tumor cells on day 0 and preincubated for 24 h. After that, the compound according to the invention is added to the cells at five concentrations, which are in each case diluted 10-fold starting from the highest soluble concentration. This is then followed by a 48-hour incubation at the end of which the cells are fixed in situ, washed and dried. Sulforhodamine B (SRB), a pink dye which is bound to the fixed cells, is then added and the cells are washed once again. The dye which remains reflects the adherent cell mass and is determined spectrometrically. The data, which are gathered automatically, are evaluated by computer and lead to the following results:

b) Results b1) For the amphiphilic compound arabinocytidylyl-(5'→1)-2-O-octadecyl-rac-glyceryly-(3→5')-5-fluoro-2'desoxyuridine according to the invention (NSC 698688-A/1)

In-vitro test results obtained with arabinocytidylyl-(5' → 1)-2-O-octadecyl-rac-glycerylyl-(3 → 5')-5-fluoro-2'-deoxyuridine (NSC 698688-A/1)

| Cell line | $GI_{50}$ in mol/l | TGI in mol/l | $LC_{50}$ in mol/l |
|---|---|---|---|
| Leukemia | | | |
| CCRF-CEM | 1.28E − 06 | >1.00E − 04 | >1.00E − 04 |
| HL-60(TB) | 3.66E − 06 | >1.00E − 04 | >1.00E − 04 |
| K-562 | 3.35E − 06 | >1.00E − 04 | >1.00E − 04 |
| MOLT-4 | 4.67E − 07 | >1.00E − 04 | >1.00E − 04 |
| RPMI-8226 | 1.65E − 06 | >1.00E − 04 | >1.00E − 04 |
| SR | — | >1.00E − 04 | >1.00E − 04 |
| Lung cancer | | | |
| A549/ATCC | 3.46E − 07 | >1.00E − 04 | >1.00E − 04 |
| EKVX | >1.00E − 04 | >1.00E − 04 | >1.00E − 04 |
| HOP-62 | 6.99E − 07 | >1.00E − 04 | >1.00E − 04 |
| HOP-92 | 8.02E − 08 | 8.99E − 05 | >1.00E − 04 |
| NCI-H226 | 7.59E − 05 | >1.00E − 04 | >1.00E − 04 |
| NCI-H23 | 7.23E − 06 | >1.00E − 04 | >1.00E − 04 |
| NCI-H322M | 3.56E − 05 | >1.00E − 04 | >1.00E − 04 |
| NCI-H460 | 4.66E − 08 | 2.79E − 05 | >1.00E − 04 |
| NCI-H522 | 1.62E − 05 | >1.00E − 04 | >1.00E − 04 |
| Intestinal cancer | | | |
| COLO205 | 1.05E − 05 | 3.88E − 05 | >1.00E − 04 |
| HCC-2998 | 5.88E − 08 | 3.50E − 05 | >1.00E − 04 |
| HCT-116 | 4.90E − 06 | >1.00E − 04 | >1.00E − 04 |
| HCT-15 | 1.44E − 05 | >1.00E − 04 | >1.00E − 04 |
| HT29 | 1.25E − 05 | >1.00E − 04 | >1.00E − 04 |
| KM12 | 7.47E − 05 | >1.00E − 04 | >1.00E − 04 |
| SW-620 | 6.28E − 05 | >1.00E − 04 | >1.00E − 04 |
| Cancer of the central nervous system | | | |
| SF-268 | 7.45E − 07 | >1.00E − 04 | >1.00E − 04 |
| SF-295 | 7.99E − 07 | >1.00E − 04 | >1.00E − 04 |
| SF-539 | 4.88E − 07 | 1.03E − 05 | 8.03E − 05 |
| SNB-19 | 9.19E − 07 | 2.37E − 05 | 6.41E − 05 |
| SNB-75 | 2.04E − 05 | >1.00E − 04 | >1.00E − 04 |
| U251 | 3.14E − 06 | 2.48E − 05 | 7.38E − 05 |
| Melanoma | | | |
| LOX IMVI | 1.40E − 06 | >1.00E − 04 | >1.00E − 04 |
| MALME-3M | >1.00E − 04 | >1.00E − 04 | >1.00E − 04 |
| M14 | 3.53E − 06 | 8.62E − 05 | >1.00E − 04 |
| SK-MEL-2 | >1.00E − 04 | >1.00E − 04 | >1.00E − 04 |
| SK-MEL-28 | 5.78E − 05 | >1.00E − 04 | >1.00E − 04 |
| SK-MEL-5 | >1.00E − 04 | >1.00E − 04 | >1.00E − 04 |
| UACC-257 | 4.98E − 05 | >1.00E − 04 | >1.00E − 04 |
| UACC-62 | 1.77E − 06 | >1.00E − 04 | >1.00E − 04 |
| Ovarian cancer | | | |
| IGROV1 | 1.36E − 05 | >1.00E − 04 | >1.00E − 04 |
| OVCAR-3 | >1.00E − 04 | >1.00E − 04 | >1.00E − 04 |
| OVCAR-4 | 5.85E − 05 | >1.00E − 04 | >1.00E − 04 |
| OVCAR-5 | 8.96E − 05 | >1.00E − 04 | >1.00E − 04 |
| OVCAR-8 | 9.68E − 07 | >1.00E − 04 | >1.00E − 04 |
| SK-OV-3 | 3.63E − 05 | >1.00E − 04 | >1.00E − 04 |
| Kidney cancer | | | |
| 768-0 | 8.54E − 07 | 1.34E − 05 | 4.44E − 05 |
| A498 | 3.19E − 07 | >1.00E − 04 | >1.00E − 04 |
| ACHN | 4.66E − 07 | >1.00E − 04 | >1.00E − 04 |
| CAKI-1 | 1.04E − 05 | >1.00E − 04 | >1.00E − 04 |
| RXF 393 | 1.02E − 05 | 2.86E − 05 | 8.00E − 05 |
| SN12C | 1.33E − 05 | >1.00E − 04 | >1.00E − 04 |
| TK-10 | 2.29E − 05 | >1.00E − 04 | >1.00E − 04 |
| UO-31 | 2.13E − 05 | >1.00E − 04 | >1.00E − 04 |
| Prostate cancer | | | |
| PC-3 | 1.15E − 05 | 8.64E − 05 | >1.00E − 04 |
| DU-145 | 2.68E − 06 | >1.00E − 04 | >1.00E − 04 |
| Breast cancer | | | |
| MCF7 | 1.70E − 07 | >1.00E − 04 | >1.00E − 04 |
| NCI/ADR-RES | — | >1.00E − 04 | >1.00E − 04 |
| MDA-MB-231/ATCC | >1.00E − 04 | >1.00E − 04 | >1.00E − 04 |

-continued

In-vitro test results obtained with arabinocytidylyl-(5' → 1)-
2-O-octadecyl-rac-glycerylyl-(3 → 5')-5-fluoro-2'-deoxyuridine
(NSC 698688-A/1)

| Cell line | GI$_{50}$ in mol/l | TGI in mol/l | LC$_{50}$ in mol/l |
|---|---|---|---|
| HS 578T | >1.00E − 04 | >1.00E − 04 | >1.00E − 04 |
| MDA-MB-435 | 3.38E − 05 | >1.00E − 04 | >1.00E − 04 |
| MDA-N | >1.00E − 04 | >1.00E − 04 | >1.00E − 04 |
| BT-549 | 1.45E − 05 | 8.69E − 05 | >1.00E − 04 |
| T-47D | >1.00E − 04 | >1.00E − 04 | >1.00E − 04 |

On the basis of the above in-vitro test results, this active compound is preferably suitable for the therapy of tumors of the lung, of the intestine, of the central nervous system and of the kidney.

b2) For the non-amphiphilic compound 2',3'-didesoxycytidylyl-(5'→1)-racglycerylyl-(3→5')-5-fluoro-2'-desoxyuridine according to the invention (NSC 704533):

In-vitro test results for 2',3'-didesoxycytidylyl-(5' → 1)-
rac-glycerylyl-(3 → 5')-5-fluoro-2'-desoxyuridin
(NSC 704533)

| Cell line | GI$_{50}$ in mol/l | TGI in mol/l | LC$_{50}$ in mol/l |
|---|---|---|---|
| Leukemia | | | |
| CCRF-CEM | — | >1.00E − 04 | >1.00E − 04 |
| HL-60 (TB) | 7.15E − 08 | >1.00E − 04 | >1.00E − 04 |
| K-562 | 2.57E − 06 | >1.00E − 04 | >1.00E − 04 |
| MOLT-4 | 1.04E − 07 | >1.00E − 04 | >1.00E − 04 |
| RPMI-8226 | 1.10E − 05 | >1.00E − 04 | >1.00E − 04 |
| SR | <1.00E − 08 | >1.00E − 04 | >1.00E − 04 |
| Lung cancer | | | |
| A549/ATCC | 4.77E − 08 | >1.00E − 04 | >1.00E − 04 |
| EKVX | >1.00E − 04 | >1.00E − 04 | >1.00E − 04 |
| HOP-62 | 9.02E − 07 | >1.00E − 04 | >1.00E − 04 |
| NCI-H226 | >1.00E − 04 | >1.00E − 04 | >1.00E − 04 |
| NCI-H23 | 9.79E − 08 | >1.00E − 04 | >1.00E − 04 |
| NCI-H322M | 1.95E − 06 | >1.00E − 04 | >1.00E − 04 |
| NCI-H460 | <1.00E − 08 | >1.00E − 04 | >1.00E − 04 |
| NCI-H522 | 7.46E − 07 | >1.00E − 04 | >1.00E − 04 |
| Intestinal cancer | | | |
| COLO 205 | 1.77E − 05 | >1.00E − 04 | >1.00E − 04 |
| HCT-116 | 3.74E − 07 | >1.00E − 04 | >1.00E − 04 |
| HCT-15 | 1.79E − 05 | >1.00E − 04 | >1.00E − 04 |
| HT29 | 1.88E − 06 | >1.00E − 04 | >1.00E − 04 |
| KM12 | 1.45E − 05 | >1.00E − 04 | >1.00E − 04 |
| SW-620 | >1.00E − 04 | >1.00E − 04 | >1.00E − 04 |
| Cancer of the central nervous system | | | |
| SF-268 | <1.00E − 08 | >1.00E − 04 | >1.00E − 04 |
| SF-295 | 3.45E − 08 | >1.00E − 04 | >1.00E − 04 |
| SF-539 | 2.16E − 08 | >1.00E − 04 | >1.00E − 04 |
| SNB-19 | 2.50E − 07 | >1.00E − 04 | >1.00E − 04 |
| SNB-75 | 1.59E − 06 | >1.00E − 04 | >1.00E − 04 |
| U251 | 1.26E − 06 | >1.00E − 04 | >1.00E − 04 |
| Melanoma | | | |
| LOX IMVI | 1.01E − 08 | >1.00E − 04 | >1.00E − 04 |
| MALME-3M | >1.00E − 04 | >1.00E − 04 | >1.00E − 04 |
| M14 | 2.03E − 07 | >1.00E − 04 | >1.00E − 04 |
| SK-MEL-2 | 7.94E − 05 | >1.00E − 04 | >1.00E − 04 |
| SK-MEL-28 | 3.79E − 05 | >1.00E − 04 | >1.00E − 04 |
| SK-MEL-5 | 6.89E − 07 | >1.00E − 04 | >1.00E − 04 |
| UACC-257 | >1.00E − 04 | >1.00E − 04 | >1.00E − 04 |
| UACC-62 | 5.50E − 07 | >1.00E − 04 | >1.00E − 04 |
| Ovarian cancer | | | |
| IGROV1 | 6.80E − 05 | >1.00E − 04 | >1.00E − 04 |
| OVCAR-3 | 6.54E − 05 | >1.00E − 04 | >1.00E − 04 |

-continued

In-vitro test results for 2',3'-didesoxycytidylyl-(5' → 1)-
rac-glycerylyl-(3 → 5')-5-fluoro-2'-desoxyuridin
(NSC 704533)

| Cell line | GI$_{50}$ in mol/l | TGI in mol/l | LC$_{50}$ in mol/l |
|---|---|---|---|
| OVCAR-4 | >1.00E − 04 | >1.00E − 04 | >1.00E − 04 |
| OVCAR-5 | 1.26E − 05 | >1.00E − 04 | >1.00E − 04 |
| OVCAR-8 | 1.41E − 07 | >1.00E − 04 | >1.00E − 04 |
| SK-OV-3 | 4.43E − 05 | >1.00E − 04 | >1.00E − 04 |
| Kidney cancer | | | |
| 768-0 | >1.00E − 04 | >1.00E − 04 | >1.00E − 04 |
| ACHN | <1.00E − 08 | >1.00E − 04 | >1.00E − 04 |
| CAKI-1 | 1.44E − 06 | >1.00E − 04 | >1.00E − 04 |
| RXF 393 | 5.12E − 06 | >1.00E − 04 | >1.00E − 04 |
| SN12C | 1.73E − 07 | >1.00E − 04 | >1.00E − 04 |
| TK-10 | 6.25E − 06 | >1.00E − 04 | >1.00E − 04 |
| Prostate cancer | | | |
| PC-3 | 2.28E − 06 | >1.00E − 04 | >1.00E − 04 |
| DU-145 | 1.58E − 07 | >1.00E − 04 | >1.00E − 04 |
| Breast cancer | | | |
| NCI/ADR-RES | 6.95E − 07 | >1.00E − 04 | >1.00E − 04 |
| MDA-MB-231/ATCC | 9.55E − 05 | >1.00E − 04 | >1.00E − 04 |
| HS 578T | 7.32E − 07 | >1.00E − 04 | >1.00E − 04 |
| MDA-MB-435 | 4.76E − 06 | >1.00E − 04 | >1.00E − 04 |
| MDA-N | 2.54E − 05 | >1.00E − 04 | >1.00E − 04 |
| BT-549 | 4.15E − 06 | >1.00E − 04 | >1.00E − 04 |
| T-47D | 1.42E − 06 | >1.00E − 04 | >1.00E − 04 |

On the basis of the above in-vitro test results, this active compound is preferably suitable for the therapy of tumors of the lung, of the central nervous system, of the kidney and of the breast, and also for treating melanomas.

What is claimed is:

1. A compound of the formula I,

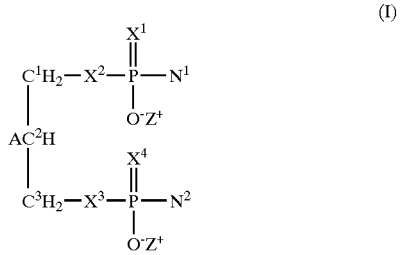

in racemic or enantiomerically pure form,
in which
the radical A and the two phosphorus-containing radicals are linked, in any arbitrary sequence, to the C atoms $C^1$, $C^2$ and $C^3$ of the glycerol backbone;
wherein each of said C atoms carries one of said radicals;
$X^1$, $X^2$, $X^3$ and $X^4$ are identical or different and, independently of each other, are oxygen or sulfur;
A is alkyl, hydroxyl, mercapto, alkyloxy or acyloxy, where the alkyl or acyl radicals are linear or branched, possess from 1 to 24 C atoms, optionally possess up to 2 double bonds and are optionally substituted by from 1 to 3 aromatic radicals;
Z is hydrogen or the corresponding salt of the acid form of this compound;
one of the radicals $N^1$ and $N^2$ is —C(═O)—OH or a salt form thereof and the other of the radicals is the radical of a D- or L-configured nucleoside derivative; or the two radicals $N^1$ and $N^2$ are different from each other and are in each case a radical of a D- or L-configured nucleoside derivative, where the nucleoside radicals are selected from radicals of the general formulae II, III and IV

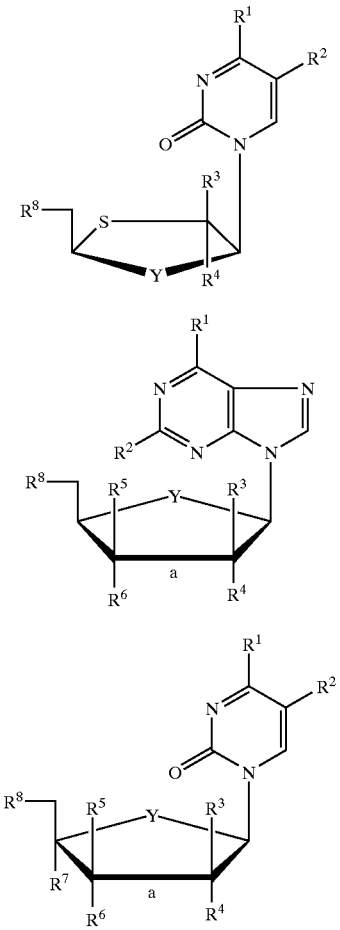

(II)

(III)

(IV)

or the tautomeric forms thereof, in which

Y is oxygen or sulfur;

$R^1$ is a hydroxyl or amino or an acylated, alkylated or polyoxyethylene-substituted amino group, whose acyl or alkyl radical is linear or branched, possesses from 1 to 24 C atoms and optionally possesses up to 2 double bonds and can be substituted by an aromatic radical;

$R^2$ is hydrogen, halogen, an amino or hydroxyl group, or a bromovinyl or a linear or branched $C_1$–$C_{24}$ alkyl radical; and $R^3$, $R^4$, $R^5$, $R^6$ and $R^7$ are identical or different and are hydrogen, halogen, hydroxyl, ethynyl or azido; the radical $R^8$ being —O— by way of which the nucleoside derivative radical is linked to the phosphorus atom, with the proviso that two of the vicinal radicals $R^3$ to $R^8$ are dispensed with when a C=C double bond is present in position a.

2. The compound as claimed in claim 1, wherein $X^1$, $X^2$, $X^3$ and $X^4$ are an oxygen atom;

the $C^1$ atom of the glycerol backbone of the formula I is linked to the radical A, where A is hydroxyl, octadecyl, octadecyloxy, docosyloxy or behenoyloxy, palmitoyl or oleoyl;

the $C^2$ atom of the glycerol backbone of the formula I is linked to $N^2$ by way of a phosphodiester bridge, where $N^2$ is a nucleoside derivative radical of the formula II, III or IV, in which Y is an oxygen atom;

$R^1$ is a hydroxyl, amino, octadecylamino, docosylamino, palmitoylamino, oleoylamino or behenoylamino;

$R^2$ is methyl, ethyl, hydrogen or halogen;

$R^3$ to $R^8$ possess the abovementioned meanings, where $R^8$ is —O— by way of which the nucleoside derivative radical $N^2$ is linked to the phosphorus atom, and the $C^3$ atom of the glycerol backbone of the formula I is linked to the hydroxycarbonylphosphonate radical in its free or salt form.

3. The compound as claimed in claim 2, wherein $N^2$ is a nucleoside derivative radical of the formula II or IV, in which $R^1$ is an amino, palmitoylamino or hydroxyl group;

$R^2$ is hydrogen, methyl or ethyl, $R^3$, $R^4$, $R^5$ and $R^7$ are hydrogen;

$R^6$ is hydrogen, fluorine or azido, and $R^8$ is an oxygen atom by way of which the $N^2$ is linked to the phosphorus atom.

4. The compound as claimed in claim 1, wherein $X^1$, $X^2$, $X^3$ and $X^4$ are —O—;

A is palmitoyloxy, oleoyloxy or octadecyloxy and is linked to the $C^2$ atom of the glycerol backbone of the formula I, and $N^1$ and $N^2$ are different and are a nucleoside derivative radical of the formulae II, III or IV.

5. The compound as claimed in claim 4, wherein $N^1$ is a nucleoside derivative radical of the formula II, in which $R^1$ is an amino or palmitoylamino group;

$R^2$, $R^3$ and $R^4$ are hydrogen, and $R^8$ is —O— by way of which the $N^1$ is linked to the phosphorus atom in position $C^1$ or $C^3$ of the glyceryl diphosphate backbone of the formula I; and $N^2$ is a nucleoside derivative radical of the formula III or IV.

6. The compound as claimed in claim 4, wherein $N^2$ is a nucleoside derivative radical of the formula IV in which $R^1$ is an amino, palmitoylamino or hydroxyl group:

$R^2$ is hydrogen or methyl;

$R^3$, $R^4$, $R^5$ and $R^7$ are hydrogen;

$R^6$ is hydrogen, fluoro or azido, and $R^8$ is —O— by way of which the $N^2$ is linked to the phosphorus atom in position $C^1$ or $C^3$ of the glyceryl diphosphate backbone of the formula I.

7. The compound as claimed in claim 4, wherein $N^1$ is a nucleoside derivative radical of the formula II or IV, and $N^2$ is a nucleoside derivative radical of the formula III, in which, in each case, $R^1$ is hydroxyl;

$R^2$ to $R^7$ are hydrogen; and $R^8$ is —O— by way of which the $N^1$ and $N^2$ are linked to the glycerol-1,3-diphosphate backbone of the formula I.

8. The compound as claimed in claim 4, wherein $N^1$ and $N^2$ are independenty a nucleoside derivative radical of the formula IV, in which, in $N^1$,
- $R^1$ is an amino, palmitoylamino or octadecylamino group;
- $R^2$, $R^5$ and $R^7$ are hydrogen;
- $R^3$, $R^4$ and $R^6$ are identical or different and are hydrogen, hydroxyl or fluoro;

and in which, in $N^2$,
- $R^1$ is a hydroxyl group;
- $R^2$ is methyl or halogen;
- $R^3$, $R^4$, $R^5$ and $R^7$ are hydrogen, where two vicinal radicals thereof are optionally dispensed with if a double bond is present in position a; and
- $R^6$ is hydrogen, fluoro, azido or hydroxyl; and
- $R^8$ in $N^1$ and $N^2$ is in each case —O— by way of which the $N^1$ and $N^2$ are linked to the glycerol-1,3-diphosphate backbone.

9. The compound as claimed in claim 8,
in which, in $N^1$ and $N^2$,
- $R^1$ is identical or different and is a hydroxyl group or an amino group;
- $R^2$ is identical or different and is hydrogen or methyl;
- $R^4$, $R^5$ and $R^7$ are hydrogen;
- $R^6$ is azido in $N^1$ and fluoro in $N^2$; and
- $R^8$ is —O— by way of which $N^1$ and $N^2$ are linked to the glycerol-1,3 diphosphate backbone.

10. The compound as claimed in claim 8,
in which, in $N^1$,
- $R^1$ is an amino or palmitoylamino group,
- $R^2$ and $R^7$ are hydrogen;
- $R^3$ and $R^4$ are fluoro, hydrogen or hydroxyl,
- $R^5$ is hydrogen or an ethynyl radical,
- $R^6$ is hydroxyl, and in which, in $N^2$,
- $R^1$ is hydroxyl,
- $R^2$ is fluoro,
- $R^3$, $R^4$, $R^5$ and $R^7$ are hydrogen;
- $R^6$ is hydroxyl, and
- $R^8$ in $N^1$ and $N^2$ is in each case —O— by way of which $N^1$ and $N^2$ are linked to the glycerol-1,3 diphosphate backbone.

11. A compound selected from
a) 3'-azido-2',3'-dideoxythymidylyl-(5'-2)-1-O-octadeyl-rac-glycerol-3 (hydroxycarbonyl)phosphonate;
b) arabinocytidylyl-(5'→1)-2-O-octadecyl-rac-glyceryfyl-(3→5')-5-fluoro-2' deoxyuridine;
c) $N^4$-palmitoyl-3'-thia-2',3'-dideoxycytidylyl-(5'→1)-2-O-octadecyl-racglycerylyl-(3→5') 3'-azido-2',3'dideoxythymidine;
d) 3'-azido-2',3'-dideoxythymidylyl-(5'→1)-2-O-octadecyl-rac-glycerylyl-(3→5') $N^4$-palmitoyl-2',3'-dideoxycytidine;
e) $N^4$-palmitoyl-2',3'-dideoxycytidylyl-(5'→1)-2-O-palmitoyl-rac-glycerylyl-(3→5') 3'-azido-2',3'dideoxythymidine;
f) 3'-azido-2',3'-dideoxythymidyiyl-(5'→1)-2-O-octadecyl-rac-glycerylyl-(3→5') 2',3'-dideoxyinosine;
g) 3'-fluoro-2',3'-dideoxythymidylyl-(5'→1)-2-O-octadecyl-rac-glycerytyl-(3→5')-3'-azido-2',3'-dideoxythymidine; and
h) 2',3'-dideoxycytidylyl-(5'→1)-raclyceryfyl-(3→5')-5-fluoro-2'-deoxyuridine;

or pharmaceutically acceptable salts of said compounds.

12. A pharmaceutical composition, comprising a compound as claimed in claim 1 in a pharmaceutically acceptable carrier or diluent, where appropriate in combination with a pharmaceutically acceptable formulating agent or incorporated into pharmaceutically acceptable liposomes or nanoparticles.

13. A method of treating HIV infections and/or cancer diseases which method comprises administering a patient a compound of claim 1; with the proviso that said cancer is selected from the group consisting of leukemia, lung cancer, intestinal cancer, melanoma, ovarian cancer, kidney cancer, prostate cancer and breast cancer.

14. The compound of claim 5, wherein $N^2$ is an L-configured nucleoside derivative radical.

* * * * *